US011890016B2

(12) United States Patent
Ad-El et al.

(10) Patent No.: US 11,890,016 B2
(45) Date of Patent: Feb. 6, 2024

(54) ANASTOMOSIS ASSEMBLY

(71) Applicant: LYDUS MEDICAL LTD., Raanana (IL)

(72) Inventors: Dean Ad-El, Mazor (IL); Kamal Daas, Tira (IL); Muhamad Mansur, Tira (IL)

(73) Assignee: LYDUS MEDICAL LTD., Raanana (IL)

( * ) Notice: Subject to any disclaimer, the term of this patent is extended or adjusted under 35 U.S.C. 154(b) by 0 days.

(21) Appl. No.: 15/733,373

(22) PCT Filed: Jan. 16, 2019

(86) PCT No.: PCT/IL2019/050061
§ 371 (c)(1),
(2) Date: Jul. 15, 2020

(87) PCT Pub. No.: WO2019/142185
PCT Pub. Date: Jul. 25, 2019

(65) Prior Publication Data
US 2020/0337707 A1 Oct. 29, 2020

(30) Foreign Application Priority Data
Jan. 16, 2018 (IL) .......................................... 256954

(51) Int. Cl.
*A61B 17/11* (2006.01)
*A61B 17/06* (2006.01)
(52) U.S. Cl.
CPC .... *A61B 17/1128* (2013.01); *A61B 17/06066* (2013.01); *A61B 2017/0608* (2013.01); *A61B 2017/1107* (2013.01); *A61B 2017/1132* (2013.01)

(58) Field of Classification Search
CPC ............ A61B 17/11; A61B 2017/0608; A61B 17/1128; A61B 17/04; A61B 17/00; A61B 2017/1103–111; A61B 2017/1117–1142; A61B 2017/047–048; A61B 17/0482; A61B 2017/06071
See application file for complete search history.

(56) References Cited

U.S. PATENT DOCUMENTS

| 3,265,069 A | 8/1966 | Healey, Jr. et al. |
| 4,553,543 A * | 11/1985 | Amarasinghe ..... A61B 17/2812 606/153 |
| 4,744,362 A | 5/1988 | Grundler |
| 5,330,503 A | 7/1994 | Yoon |
| 5,417,699 A | 5/1995 | Klein et al. |

(Continued)

FOREIGN PATENT DOCUMENTS

| GB | 2537878 A | 11/2016 |
| WO | 2016/030877 A1 | 3/2016 |
| WO | 2016/128961 A2 | 8/2016 |

*Primary Examiner* — Kathleen S Holwerda
*Assistant Examiner* — Serenity A Miller
(74) *Attorney, Agent, or Firm* — Vorys, Sater, Seymour and Pease LLP; Anthony P. Venturino; Maryellen Feehery Hank

(57) ABSTRACT

Provided is a device for use in anastomosis particularly (although not exclusively) suitable for anastomosis of tubular organs within the body, particularly small tubular organs (such as blood vessels, bile duct, lymph duct, nerve ducts, epididymis, etc.).

10 Claims, 13 Drawing Sheets

(56) References Cited

U.S. PATENT DOCUMENTS

| | | | |
|---|---|---|---|
| 5,554,162 A * | 9/1996 | DeLange | A61B 17/0469 |
| | | | 606/153 |
| 5,746,757 A | 5/1998 | McGuire | |
| 6,042,583 A * | 3/2000 | Thompson | A61F 2/0031 |
| | | | 606/232 |
| 6,280,460 B1 | 8/2001 | Bolduc et al. | |
| 6,682,540 B1 * | 1/2004 | Sancoff | A61B 17/115 |
| | | | 606/153 |
| 2002/0077636 A1 * | 6/2002 | Arcia | A61B 17/11 |
| | | | 606/139 |
| 2003/0158562 A1 | 8/2003 | Feigl | |
| 2004/0199185 A1 | 10/2004 | Davignon | |
| 2005/0288697 A1 | 12/2005 | Tei et al. | |
| 2006/0167485 A1 | 7/2006 | Blatter | |
| 2011/0087253 A1 | 4/2011 | Paz et al. | |
| 2011/0306994 A1 * | 12/2011 | Bassan | A61B 17/0469 |
| | | | 606/153 |

\* cited by examiner

ANASTOMOSIS ASSEMBLY

TECHNOLOGICAL FIELD

The present disclosure concerns a device for use in anastomosis, particularly (although not exclusively) suitable for anastomosis of tubular organs within the body, particularly small tubular organs (such as blood vessels, bile duct, lymph duct, nerve ducts, epididymis, etc.).

BACKGROUND ART

References considered to be relevant as background to the presently disclosed subject matter are listed below:
 WO 2016/128961
 U.S. Pat. No. 4,744,362
 US 2006/0167485
 US 2004/0199185
 U.S. Pat. No. 5,330,503
 US 2005/0288697
 U.S. Pat. No. 5,746,757
 U.S. Pat. No. 5,417,699
 U.S. Pat. No. 3,265,069

Acknowledgement of the above references herein is not to be inferred as meaning that these are in any way relevant to the patentability of the presently disclosed subject matter.

BACKGROUND

Various techniques are known in medical practice for the anastomosis of severed tubular organs, including blood vessels and others. WO 2016/128961 discloses, among others, anastomosis devices for the coupling of two tubular organs, that makes use of multiple threads each with needles at its two ends, and a device that streamlines the suturing procedure intended to join the two vessel portion to one another.

GENERAL DESCRIPTION

Provided by this disclosure is an assembly for use in an anastomosis procedure (referred to herein as an "anastomosis assembly") for joining together cut ends of tubular organs. In the following, the cut ends may be also referred to, each, as a "stump" and the end walls of the stump as "stump walls". Such tubular organs may be blood vessels, lymph vessels, bile ducts, and others. The terms "stump" and "cut end" are used interchangeably.

The assembly of this disclosure comprises a combination of elements intended to streamline an anastomosis procedure and allow it to be concluded relatively rapidly and efficiently. In particular, the assembly of this disclosure is intended to guide the suturing needle to pierce through the stump walls, pulling the suturing thread with it. By some embodiments of this disclosure, each suturing needle is guided to penetrate successively through both opposite stump walls, pulling a common suturing thread through the opposite walls. By other embodiments, the suturing needles are provided in pairs, to form together with a suturing thread that joins their two rear portions, a suturing unit. One needle of the pair is guided to penetrate through one stump wall and the other through the walls of the opposite stump, thereby pulling the suturing thread through the stump walls. Once two opposite stumps are so threaded, the two stumps can be efficiently joined together. The assembly of this disclosure thus includes a device configured for such guidance, as well as suturing needles linked to threads at their rear portion, which may either be a priori incorporated and accommodated within guiding channels formed in the device, or provided separately, e.g. as a part of a kit including said device and needles linked to suturing threads or such suturing units and configured for insertion in guiding channels within the device. The guiding channels are typically curved, and the suturing needles may be curved in a corresponding manner. The suturing needles may also be made elastic to permit them to bend to match the channel's curvature.

Also provided by this disclosure are such devices, suturing needles and suturing units for use in the disclosed assemblies.

Provided by this disclosure is also a kit of parts for assembling an anastomosis assembly of this disclosure. The kit may comprise the assembly, parts of the assembly intended to be put together before the procedure and/or or the suturing units. Provided by this disclosure is also a suturing unit configured for use in the assembly of this disclosure.

The anastomosis assembly of this disclosure, for joining one stump of a cut tubular organ to another, comprises a device having a body with two opposite axial projections extending therefrom. Each of these is configured for coupling with the stump such that the walls of the stump can be pulled over the external projection to cover a stump-engaging portion thereof.

The state of engagement where the stump rests over the stump-engaging portion will be referred here at times as "suturing state". The terms "axis" or "axial" will be used to denote the axis defined by and extending between these projections and also, depending on the context, a direction generally parallel thereto.

A plurality of curved guiding channels (e.g. 2, 3, 4, 5, 6, 7, 8 or even more) are formed in the device, each of which extends in a general axial direction between a first end thereof and a second end which is defined in a stump-engaging portion of one of the axial projections. The guiding channel is configured for receiving a suturing needle, that has a pointed front portion and a rear portion linked to a suturing thread, and guiding it to pierce through stump walls. By some embodiments the suturing needles may be a priori incorporated into the guiding channels. By other embodiments they are provided separately, e.g. as part of a kit, and introduced into the guiding channels prior or during the anastomosis procedure.

By one embodiment, each of the guiding channels extends between a stump-engaging portion of one axial projection to a stump-engaging portion of the other. By another embodiment, each of the guiding channels extends between the body and a stump-engaging portion. In the case of said one embodiment, a suturing element including a single suturing needle linked to a suturing thread is used and is guided to pierce the stump walls from the exterior of one of the stumps and then passes through the guiding channel to pierce the inside walls of the opposite stump of the opposite stump. In the case of said other embodiment, a suturing unit (including, as defined above, two suturing needles linked by a common suturing thread) is used, both guided by the guiding channel to pierce through the stump wall of one of the two opposite stumps which causes the suturing thread to then extend between the stumps.

The device in the assembly of this disclosure is typically axial symmetric with two opposite axial projections extending from a central body. The device may also have a mirror symmetry about a plane perpendicular to the axis. However, the mirror symmetry is not obligatory and other configurations of the device without a mirror symmetry are also possible; for example, a device with two different axial projections, differing from one another in their diameters and, hence, intended for use in anastomosis of vessel stumps of different diameters. The axial projections are, typically, generally cylindrical, conical or frusto-conical and may also have a tapered end.

Each axial channel that extends into one of the two axial projections has an opposite counterpart extending from the body into the other of the axial projections. One of the two needles of a suturing unit is then incorporated into one of these channels and the other into the opposite counterpart channel.

In an exemplary embodiment, where the two stumps are substantially of the same diameter, the two axial projections may be identical; although in some embodiments the two axial projections may be of different diameters or lengths. The axial projections have typically a general cylindrical configuration and may have a tapered end to facilitate their engagement with said stumps. It should be noted that within the framework of an anastomosis procedure, the stump walls are, as noted above, pulled over the axial projections and the tapered ends provide guiding surfaces for the walls of the tubular organ that are pulled over the axial projections' external surface. As will be noted below, the stump walls are pulled over the axial projection until the stump walls end portion comes to lie over the openings of the first tunnel (defined above as the suturing state), walls of one stump laying over the first inlet and walls of the other, opposite stump, over the first outlet.

Two non-limiting embodiments of the general teaching of this disclosure are described below. One of these is referred to as the "open channel embodiment" and the other as the "bored embodiment". As can be understood, some features described in connection with one of these embodiments may apply to the other and also to further embodiments that employ the general teaching of this disclosure.

Open Channel Embodiment

The guiding channels according to the open channel embodiment, may be open guiding channels formed as axial open channels or slits, extending down from the surface of the device between sidewalls to a bottom face. The guiding channels can receive and accommodate, as well as guide, the displacement of the suturing needles during the anastomosis procedure. An assembly of this disclosure with such open channels will be referred to herein as "open channels assembly"; and the device of such assembly as "open channel device". The bottom face of such channels is formed with a curvature for guiding the needle in the manner described above. An open channels assembly typically comprises also a retaining element that is configured for retaining the suturing needles within the open channels to permit sliding within the channel without escaping out of the open external face of the channel. The retaining element is configured for removal to eventually permit freeing the suturing thread. The open channel embodiment is particularly, although not exclusively, suitable for anastomosis of narrow vessels, e.g. small blood or lymph vessels.

The open channel device is formed, as noted above, with axially-extending and radially-oriented open channels defined between side walls and a curved bottom wall, each channel extending between one end at the central body to a second end in the stump-engaging portion of a projection. The open channel assembly also comprises a plurality of suturing units, each unit comprising a pair of suturing needles linked to one another at their rear portions by a suturing thread, each needle having a pointed front portion. Each suturing needle of a suturing unit is accommodated in a channel opposite that of the other with respect to the plane of mirror symmetry. The pointed front portion of each needle is in the direction of the second end, each of the needles being slidable within the channel guided by the bottom wall to pierce through the stump walls once pulled over the stump-engaging portion.

By one embodiment of the open channel assembly, the rear portion of the needle projects out of the first end, and through manipulation of this portion, the needle can be pushed to cause it to slide in a generally axial direction in the direction of said first end (to be referred to as "forward"). By another embodiment, the assembly comprises a sliding insert that is configured for removable insertion into said channels and engagement with the suturing needle accommodated therein and cause the needle to slide forward. The sliding insert may have the general shape of a disc having a needle-engaging edge that has a curvature matching that of the bottom wall of the channel. The needle-engaging edge of the sliding insert causes the forward sliding of the suturing needle through friction engagement, and may be fitted with a friction-increasing material or may be treated for increased friction, e.g. by texturing the surface.

The suturing needles are typically retained within the channels by a retaining element, which can be a ring or band, e.g. elastic, fitted about the device over the channels and which is typically configured for removal, e.g. by cutting or breaking, to permit freeing of the suturing threads from the device.

The channels may be configured for retaining the needles, but permitting release of the suturing thread once pulled into the channel by the advancing needle. The needle has typically a diameter exceeding that of the thread, in addition to some inherent flexibility of the thread. The open channel may, thus, be provided with bulges at a distance above the bottom face of the channel, that leave an opening between them which is narrower than the needle's diameter, thus, retaining the needle at or close to the channel's bottom between the walls and such bulges. An alternative configuration is one in which the overall width of the channel is broader than the needle's diameter, while the bottom of the channel contains a broader portion, e.g. of a general circular cross-section, that can accommodate the needle which is, in this way, retained at the channel's bottom. The thread, however, which has a diameter smaller than that of the distance between the bulges or the general width of the channel, as the case may be, can thus be freed from the channel. In some embodiments, where the thread has a diameter similar to that of the needle, it may nonetheless be freed from the channel by virtue of its flexibility.

The Bored Embodiment

The guiding channels according to the bored embodiment are in the form of bores defined within the device. The bores may, by some embodiments, be formed by matching recesses defined in opposite faces of elements that are joined together to form the device in a manner to permit them to be disintegrated, to thereby free the thread that becomes accommodated within the bore after being pulled thereinto by the needle. An assembly of this disclosure with bores as the guiding channels will be referred to herein as "bored assembly"; and the device of such assembly as "bored device".

The bored assembly comprises a central body with two opposite axial projections of the kind described above with respect to the open channels embodiment. Tunnel are formed in the central body and comprise two or more first tunnels (typically 4, 5, 6, 7, 8 or at times even more), that extend in a general axial direction between openings at opposite sides of the central part, one opening being formed at the stump-engaging portion of one of the projections and the other at the stump-engaging portion of the opposite projection. Each of the tunnels is configured for receiving and guiding one suturing needle of a suturing unit (the suturing unit comprising the needle and suturing thread coupled to its rear portion), to pierce walls of opposite stumps fitted over the stump-engaging portions. The assembly is configured for disintegration to thereby expose the entire length of the first tunnels. Each of the first tunnels is typically curved such that its two openings open in a corresponding radial configuration, each on an opposite side of the central part. When the stump walls are pulled over the stump-engaging portions of the axial projections and are in their suturing state, the end portions of the stump walls come to lay over said openings, and the suturing needle can be guided to penetrate into one of the openings of the first tunnel, referred to herein as "first inlet". The needle is then guided by the first tunnel to egress out of the opening at the tunnel's other end, referred to herein as "first outlet". When in the suturing state, the guided movement of the needle causes it to penetrate through the end portions of the stump walls. The device is configured for disintegration, and after its disintegration the suturing threads that were pulled by the needles can form sutures for joining the two stumps to one another. A plurality of such sutures may be formed by guiding a plurality of suturing units in that manner, or successively guiding one needle through a succession of such first tunnels (see below regarding definition of pairs of tunnels), to thereby join two cut ends to one another.

As noted above, the bored assembly is configured for disintegration. Following the guided suturing (in the manner noted above and further explained and exemplified in connection with some embodiments further below), the bored assembly is disintegrated, thereby fully exposing the tunnels and the portion of the suturing units that is within the tunnels; and through pulling of the suturing threads, the two stumps can then be manipulated into proximity and sutured to one another.

This needle guidance procedure is enabled, by embodiments of the bored assembly of this disclosure, through a combination of tunnels, including a plurality of first tunnels, as defined above, and a plurality of corresponding tunnels referred to herein as "second tunnels". Each first tunnel and its corresponding second tunnel constitute together a pair of tunnels, namely a "tunnels' pair".

Each of the first and second tunnels has one opening that, in relation to the needle's point of entry and passage through the tunnel, is referred to herein as "inlet" and the other as "outlet" (the needle passing through the tunnel in the direction from the inlet to the outlet). In some embodiments, the assembly is mirror-symmetric about a plane normal to the axis and the inlet and outlet of the tunnel are indistinguishable from one another; one serving as the inlet and the other serving as the outlet, depending on the needle's direction. The terms inlet and outlet will be used for convenience throughout this description, it being understood that these terms may, but often do not signify any structural difference.

The device of this embodiment typically comprises a generally axial core member and an external body. The core member is an elongated member with a central segment defined between two peripheral segments which form the axial projections.

The external body is formed around said central segment and is tightly associated therewith, constituting together a central part, said axial projections axially projecting therefrom.

In some embodiments, plurality of first tunnels are defined between the central segment and surrounding portions of the external body, each tunnel extending between the first inlet and the first outlet. The first inlet and first outlet are axially separated from one another, one being at the interface between one axial projection and the central segment, and the other being at the interface between the central segment and the other of the axial projections. Each of the first tunnels may be formed by means of a groove on the surface of the central segment, or a groove formed on the inner-facing surface of the external body that overlays the central segment. The first tunnels being formed between such grooves and the opposite surface, or grooves may be formed on both these opposite surfaces; the first tunnels being formed upon joining of the two grooves, and in the event of two opposite grooves, also proper alignment is obtained.

In the case where the tunnels are part of a tunnels' pair, formed in said external body are a plurality of second tunnels, each extending between two openings—referred to herein as "second inlet" and "second outlet". As noted above, each first tunnel has a corresponding second tunnel, together constituting the tunnels' pair. Each of said second tunnels is configured to receive a suturing needle of a suturing unit, in a manner that permits the needle's extraction through the second outlet in a trajectory that guides the needle's tip to penetrate the corresponding first tunnel of the tunnels' pair through the first inlet, to eventually extract out of the first outlet. Thus, a suturing needle passing through a tunnel's pair is continuous within at least the second or the first tunnel until it is extracted out of the first outlet.

Said external body is configured for disintegration from the core member and such disintegration leads to exposure of the entire length of the first tunnels and thereby frees that part of the suturing unit contained therein.

The plurality of tunnels' pairs, which may consists of 3, 4, 5, 6, 7, 8, 9, 10, etc. pairs, are typically arranged in a radially symmetric manner in the assembly. This ensures substantial radial symmetry of the eventual sutures.

A plurality of suturing units may be used, typically one for each tunnels' pairs. Thus, where, for example, the assembly includes 4, 5, 6, 7, 8, 9 or 10 tunnels' pairs, a corresponding number of suturing units may be used. The needles may be a priori accommodated within the second tunnels; or may be inserted into the second tunnels, immediately before or during the anastomosis procedure, in which the assembly of the disclosure is used.

By another embodiment of this disclosure, blind holes are formed in said external body instead of the through tunnels, each blind hole functions similarly to said second tunnel (thus also having a second inlet and a second outlet defined at opposite ends of the blind hole). Each of the blind holes is configured to accommodate the suturing unit with the needle projecting out through the second outlet of the blind hole. The suturing units may be a priori accommodated within these blind holes or may be reversely inserted through the second outlets prior to or during the anastomosis procedure.

By yet other embodiments, a number of suturing units, fewer than that of the tunnels' pairs, can be used, for example, using one suturing unit. Such a suturing unit is passed in succession through the second and first tunnels of a first tunnels' pair and then through another successive pair, etc. The needles typically have a non-constrained arched shape, assumed by the needle upon extraction from the second outlet of the second tunnel and define an arched trajectory that guides the needle's tip into the first inlet of the first tunnel of the same tunnels' pair. The second tunnel may be designed to have the same curvature as the arched curvature of the needle and, in this way, the needle passes through the second tunnel in a non-constrained manner. However, it is also possible for the second tunnel to be straight or have a different curvature than the arched curvature of the needle; and then the needle, through its internal bias, assumes its non-constrained arched curvature once exiting through said second outlet.

Each first tunnel and second tunnel of the same tunnels' pair may be configured to jointly define an arch of a common circle. Thus, in this manner, the needle passes through the second and then first tunnel of a pair, in an overall trajectory that traces the circumference of such a circle.

The central segment of the core member has typically a bi-concave cross-sectional shape.

The external body typically has a generally annular shape with an internal face surrounding a void that accommodates the central segment. Thus, the internal faces of the external body has an overall shape that matches that of the central segment. Where the central segment has a bi-concave cross-sectional shape, the cross-sectional shape of the internal face of the external body will be convex with a matching curvature.

The anastomosis assembly of this embodiment may comprise an integration-retaining member that maintains integrity of the external body and that can be removed, broken, or disassembled to thereby permit disintegration. Such integration-retaining member may, for example, be a rigid or flexible ring, retained within a groove formed on the peripheral face of the external body. The external body may be made of a plurality (e.g. 2, 3, 4, 5, 6, etc.) of complementary sub-units that together form said external body and that upon removal, breaking or rupturing of the retaining member that holds them together, they separate from one another, thereby disintegrating the external body.

The sub-units of the external body, each constitutes a radial section of the body and thus, upon disintegration, each one forms a unit separate from the others on another radial side of the axis.

By one embodiment, the second tunnels extend in a generally axial direction between opposite faces of the external body, between second inlet on one face and the second outlet on another. In such embodiments, the second tunnels extend in a generally axial direction. According to another embodiment, the second tunnels extend between a second inlet in the peripheral portion of the external body and a second outlet at space proximal to said core member, thus the second tunnels extend in an overall radial orientation.

Typically, although not exclusively, the assembly comprises a radially directed, diverging surface formed at the interface between the axial projection and the external body. By one embodiment, the diverging surface is a slanted surface that diverges in the peripheral-to-central direction and is defined by one or both of a portion of the core member and a portion of the external body. Typically, such a slanted surface is formed by a combination of a portion of the core member and a portion of the external body, whereby the openings of the first tunnel are defined in a mid-portion of the slanted surface.

Embodiments

Listed below in the following numbered paragraphs are certain embodiments of this disclosure. The list of embodiments is intended to illustrate and clarify the teaching of this disclosure, but is not intended to limit it in any way, as generally described above.

1. An anastomosis assembly for joining one stump of a cut tubular organ to another comprising:
   a device having a body with two opposite axial projections each of which being configured for insertion into a stump to be joined to another and to permit the stump walls to be pulled over a stump-engaging portion of the external surface of the axial projections;
   and a plurality of curved guiding channels, each of which extending in a general axial direction between a first end and a second end defined in the stump-engaging portion of one of the axial projections and configured for receiving a suturing needle, having a pointed front and a rear linked to a suturing thread, and guiding it to pierce through stump walls.

2. The assembly of embodiment 1, comprising a plurality of suturing needles a priori accommodated within the guiding channels.

3. The assembly of embodiment 1 or 2, wherein each of the guiding channels extends between a stump-engaging portion of one axial projection to a stump-engaging portion of the other.

4. The assembly of embodiment 1 or 2, wherein each of the guiding channel extends between the body and a stump-engaging portion.

The assembly of embodiment 4, wherein each of the guiding channels accommodates a suturing needle.

6. The assembly of any one of the preceding embodiments, wherein said device has an axial symmetry.

7. The assembly of any one of the preceding embodiments, wherein said device has a mirror symmetry about a plane perpendicular to the axis.

8. The assembly of embodiment 7, wherein each of the guiding channels extends between the body and a stump-engaging portion and accommodates a suturing needle with a suturing thread extends between needles in opposite guiding channels.

9. The assembly of any one of the preceding embodiments, wherein each of the guiding channels is a bore.

The assembly of any one of embodiments 1-8, wherein each of the guiding channels is formed as an open channel.

11. The assembly of embodiment 10, comprising a retaining element configured for retaining the suturing needles within the open channel.

12. The assembly of embodiment 11, wherein the retaining element is removable to permit freeing of the suturing needle.

13. The assembly of embodiment 11, wherein the open channel is configured for retaining the suturing needle but permitting release of the suturing thread.

14. The anastomosis assembly of any one of the preceding embodiments, wherein the axial projections are generally cylindrical.

The anastomosis assembly of any one of the preceding embodiments, wherein the axial projections are tapered.

16. An anastomosis assembly for joining one stump of a cut tubular organ to another comprising:
   an axial symmetric device with two opposite axial projections extending from a central body, each of the projections being configured for insertion into one of the stumps to be joined to the other and to permit the stump walls to be pulled over a stump-engaging portion of the external surface of the axial projections;
   the device being formed with axially-extending radially-oriented open channels defined between side walls and a curved bottom wall, each open channel extending from one end at the central body to a second end in the stump-engaging portion of a projection;

a plurality of suturing units, each unit comprising a pair of suturing needles linked to one another at their rear portion by a suturing thread, each needle having a pointed front portion; and each suturing needle of a suturing unit being accommodated in one of the open channels opposite, with respect to the plane of mirror symmetry to the other, with its pointed front portion in the direction of said second end, each of the needles being slidable within the channel guided by the bottom walls to pierce through the stump walls once pulled over the stump-engaging portion.

17. The assembly of embodiment 16, wherein the device has a mirror symmetry about a plane perpendicular to the axis.

18. The assembly of embodiment 16 or 17, wherein the rear portion of the needle projects out of the first end and the needle can be slid in a general axial direction by pushing said rear portion.

19. The assembly of embodiment 16 or 17, wherein sliding of the needle is achievable by means of a sliding insert insertable into the open channel.

20. The anastomosis assembly of any one of embodiments 16-19, wherein the axial projections are generally cylindrical.

21. The anastomosis assembly of any one of embodiments 16-20, wherein the axial projections are tapered.

22. The anastomosis assembly of any one of embodiments 16-21, comprising a retaining element configured for retaining the suturing needles within the open channel.

23. The assembly of embodiment 22, wherein the retaining element is removable to permit freeing of the suturing needle or the suturing thread.

24. The assembly of embodiment 23, wherein the retaining element is an elastic ring or band that is removed by severing or cutting.

25. The assembly of embodiment 22, wherein the open channel is configured for retaining the suturing needle but permitting release of the suturing thread.

26. An anastomosis assembly for joining two stumps of a cut tubular organ comprising:

a central body with two opposite, axial projections, each of which being configured for insertion into a stump to be joined to another and to permit the stump walls to be pulled over a stump-engaging portion of the external surface of the axial projections;

two or more first tunnels, that extend in a general axial direction between openings at opposite sides of the central part, one opening being formed at the stump-engaging portion of one of the projections and the other at the stump-engaging portion of the opposite projection;

each of the tunnels being configured for receiving and guiding a suturing needle of a suturing unit, each suturing unit comprising the needle and suturing thread coupled thereto, to thereby permit a suturing needled to pierce walls of opposite stumps once fitted over said stump-engaging portions; and said assembly being configured for disintegration that exposes the entire length of the first tunnels.

27. The anastomosis assembly of embodiment 26, wherein the axial projections are generally cylindrical.

28. The anastomosis assembly of embodiment 26 or 27, wherein the axial projections are tapered.

29. An anastomosis assembly for joining two stumps of a cut tubular organ comprising:

a generally axial core member with a central segment between two opposite axial projections, each axial projection being dimensioned for insertion into the opening of one of the two stumps and to permit the stump walls to be pulled over a stump-engaging portion of the external surface of the axial projections;

an external body formed around said central segment and tightly associated therewith;

plurality of tunnels' pairs each comprising a first tunnel defined between said central segment and the external body and extending between a first inlet and a first outlet, in axial separation from one another, the inlet being formed on a stump-engaging portion of one of the axial projections and the outlet being formed on the stump-engaging portion of the opposite axial projection, and comprising a second tunnel formed in the external body and extending between a second inlet and a second outlet and configured to receive a suturing needle of a suturing unit that comprises the needle and a suturing thread, in a manner to permit its extraction through the second outlet in a trajectory such that the needle will penetrate said first inlet;

the external body being configured for disintegration from the core member to thereby expose the second tunnels' entire length.

The anastomosis assembly of embodiment 29, wherein one or more of the second tunnels a priori accommodates a suturing needle.

31. The anastomosis assembly of embodiment 29 or 30, wherein the needle has a non-constrained arched shape assumed by the needle upon extraction from the second tunnel to define an arched trajectory guiding the needle's tip into the first inlet.

32. The anastomosis assembly of any one of embodiments 29-31, wherein each first tunnel and its corresponding second tunnel, defining an arch of a common circle.

33. The anastomosis assembly of any one of embodiments 29-32, wherein the central segment of the core member has a bi-concave cross-sectional shape.

34. The anastomosis assembly of any one of embodiments 29-33, wherein the external body has a generally annular shape.

The anastomosis assembly of any one of embodiments 29-34, wherein the external body comprises an integration-retaining member that maintains integrity of the external body and that can be removed, broken or disassembled to thereby permit disintegration of the external body.

36. The anastomosis assembly of embodiment 35, wherein the external body comprises a plurality of sub-units held together by the integration-retaining member.

37. The anastomosis assembly of embodiment 35 or 36, wherein the integration-retaining member is an annular member fitted around the periphery of the external body and removed by cutting or breaking.

38. The anastomosis assembly of any one of embodiments 35-37, wherein the integration-retaining member is an elastic ring accommodated within a peripheral groove.

39. The anastomosis assembly of any one of embodiments 35-38, comprising a peripheral depression configured to permit cutting of the integration-retaining member.

The anastomosis assembly of any one of embodiments 29-39, wherein the second tunnels extend between opposite faces of the external body spaced apart in a direction parallel to that of the axis.

41. The anastomosis assembly of any one of embodiments 29-39, wherein the second tunnels extend between a peripheral portion of the external body and a space proximal to said core member.

42. The anastomosis assembly of any one of embodiments 29-41, wherein each of said axial projections is cylindrical with a diameter corresponding to that of the respective stump.

43. The anastomosis assembly of any one of embodiments 29-42, wherein each of the axial projections has a tapered end.

44. The anastomosis assembly of embodiment 42 or 43, wherein the diameter of the axial projection is such that the end segment fits snugly into said cut tubular organ.

The anastomosis assembly of any one of embodiments 42-44, wherein the stump-engaging portion is a radially directed, diverging surface and positioned at an interface between the axial projection and the external body.

46. The anastomosis assembly of embodiment 45, wherein the diverging surface is a slanted surface diverging in the peripheral-to-central direction and defined by (i) a portion of said core member, (ii) a portion of said external body or by (iii) a combination of a portion of said core member and said external body.

47. A kit for assembling the anastomosis assembly of any one of embodiments 1 to 46.

48. The kit of embodiment 47, comprising the assembly of any one of embodiments 1 to 46 and one or more of said suturing units.

49. A suturing unit configured for use in the assembly of any one of embodiments 1 to 46.

A device for use in the assembly of any one of embodiments 1 to 46.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 2A-2D are isometric longitudinal cross-sections; while FIGS. 2E-2H are isometric views.

DETAILED DESCRIPTION OF EMBODIMENTS

Figure 5:
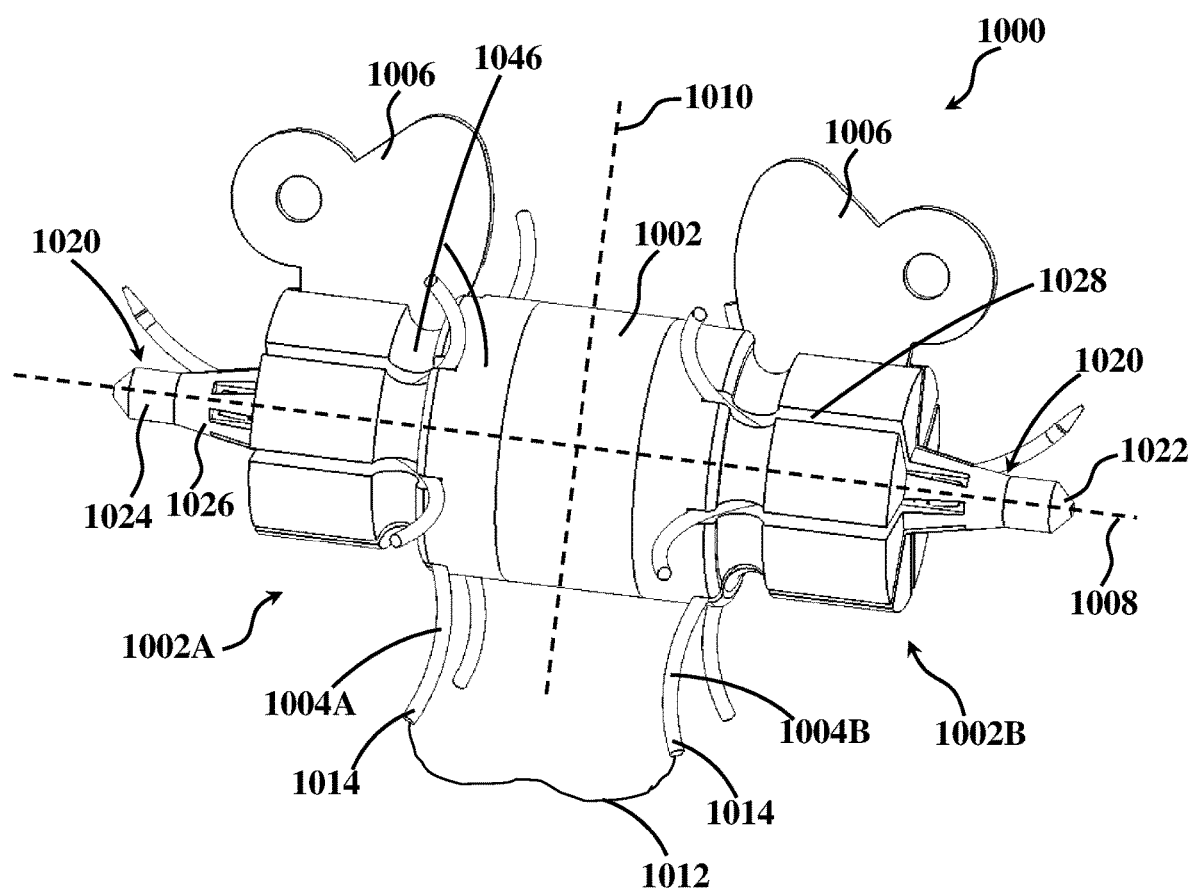
FIG. 5 is a schematic isometric view of an anastomosis assembly according to the open channel embodiment of this disclosure, coupled with sliding inserts.
Figure 6A:
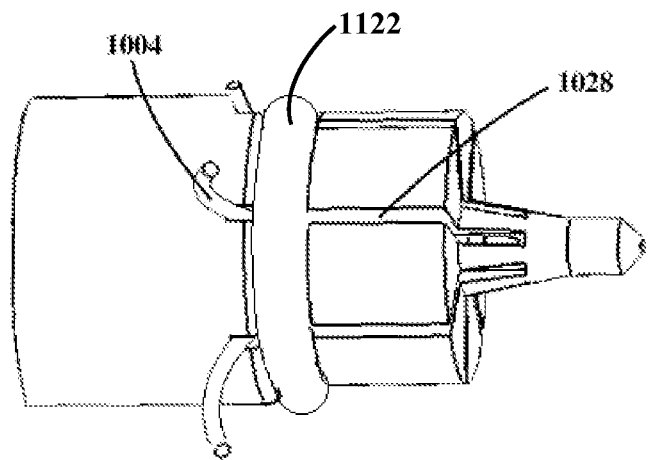
FIG. 6A shows half of the device of FIG. 5, with all of the needles being fully accommodated within the channels.
Figure 6B:
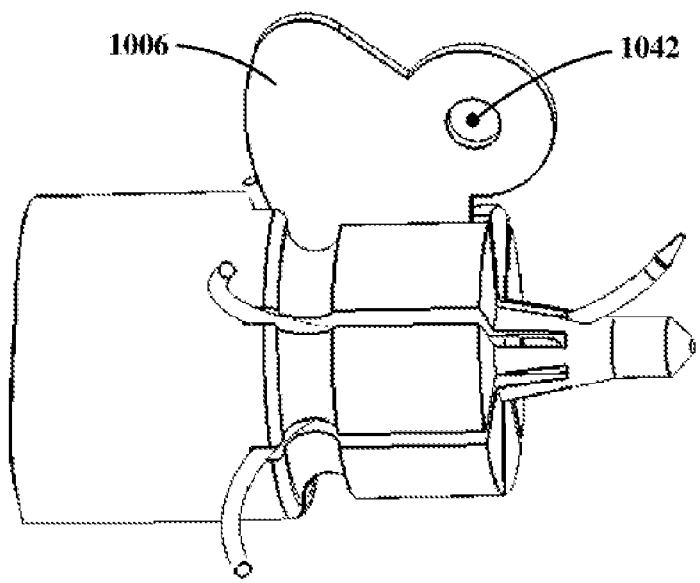
FIG. 6B shows the device of FIG. 6A with coupled with a sliding insert with one of the suturing needles partially extracted.
Figure 6C:
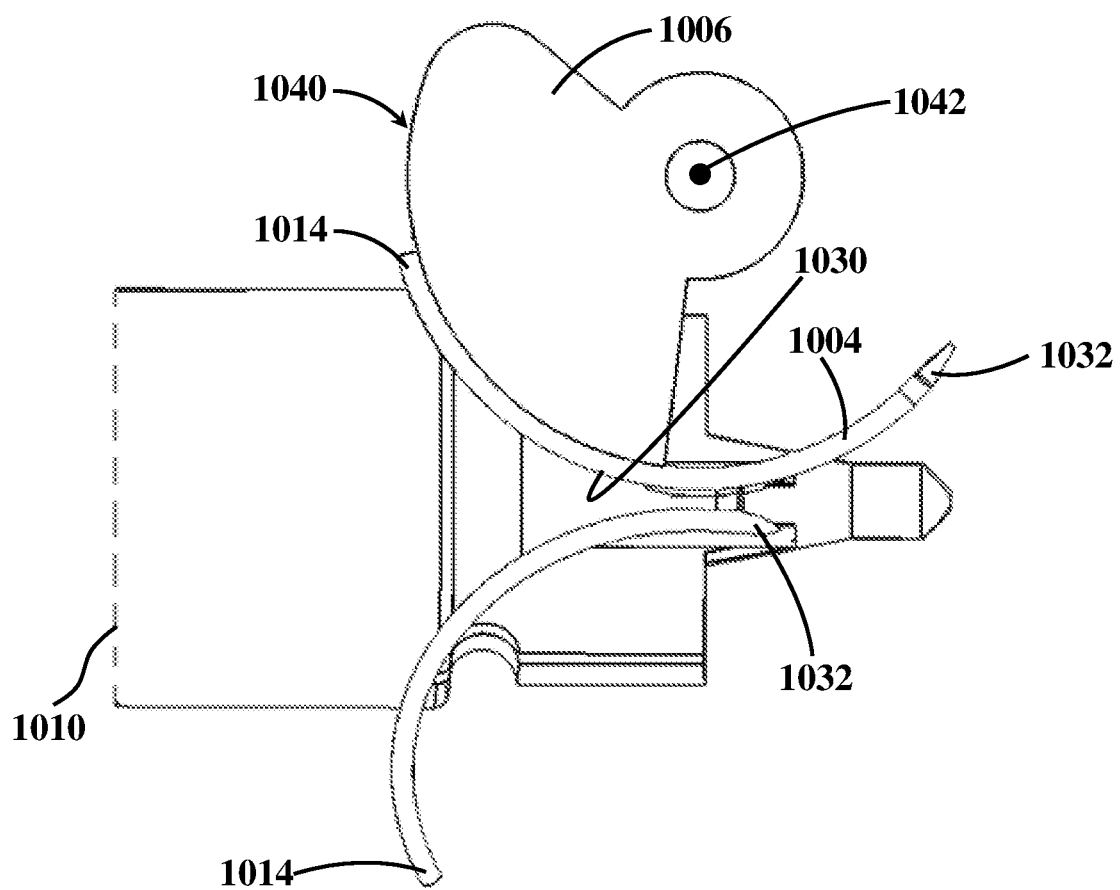
FIG. 6C is a longitudinal cross section of FIG. 6B.

The invention will now be further described with reference to the exemplary embodiments depicted in the annexed drawings. These exemplary embodiments are meant to illustrate the anastomosis assembly of this disclosure but not intended to be limiting in any way. In other words, the scope of this disclosure applies to the full contents of the above disclosure and is not limited in any way to these exemplary embodiments. Of the illustrated exemplary embodiments, those of FIGS. 1-4 are of the bored embodiment of this disclosure, while those of FIGS. 5-6C are of the open channel embodiment.

Figure 1:
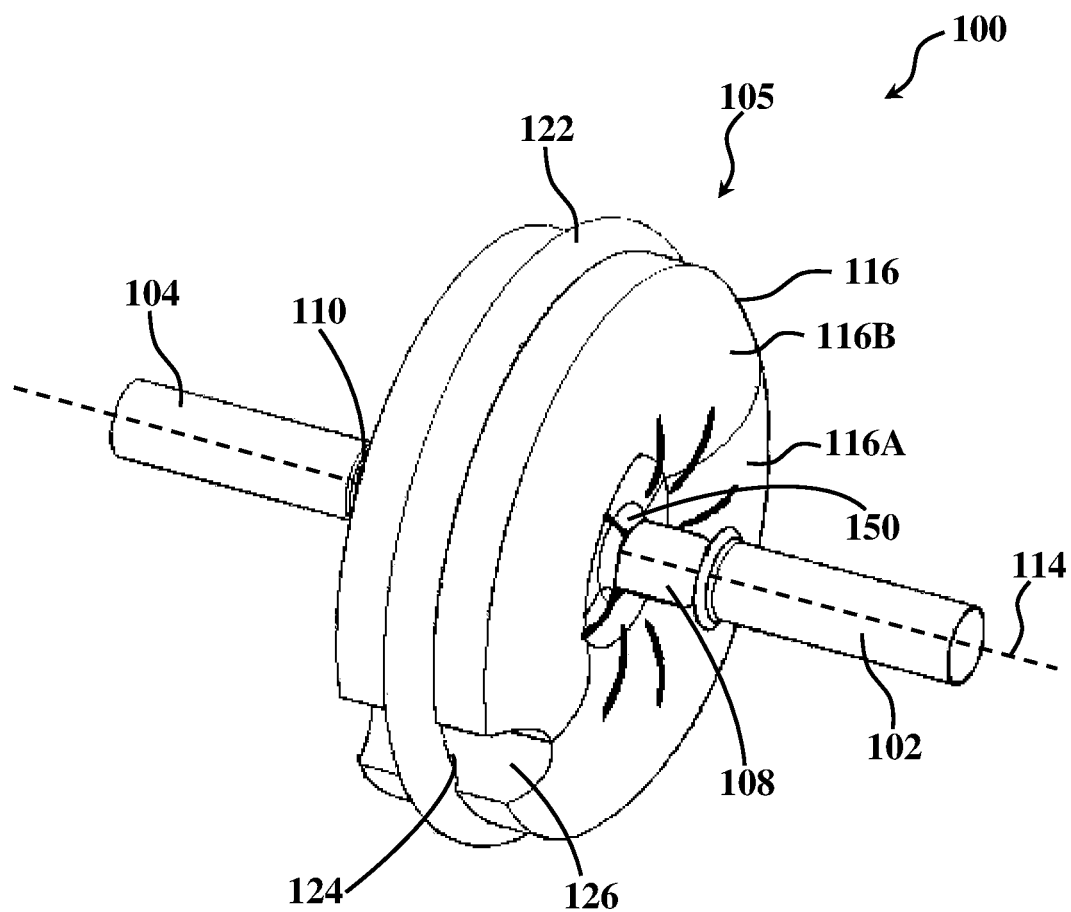
FIG. 1 is a schematic isometric view of an exemplary anastomosis assembly, according to the bored embodiment of this disclosure. In this Figure, the assembly is shown in situ, between the two stumps of a cut tubular organ.

Reference is now made to FIG. 1 showing an anastomosis assembly generally designated 100 in situ, namely positioned between two stumps 102, 104 of a cut tubular organ to be joined together (the tubular organ being cut, for example, during surgery or as a result of an accident). Assembly 100 has a central part 105 with two opposite axial projections 108, 110 which are integral with the core member 106, which, as can better be seen in FIGS. 2A-2D, is elongated and comprises also a central segment 112 therebetween. As can further best be seen in FIGS. 2A-2D, the ends 108A, 110A of the respective axial projections 108, 110 are tapered; and a central segment 112 has a bi-concave cross-section. The elongated core member 106 is orientated in a manner that defines an axis 114. In the description herein, the term axial will be used to define a direction parallel to axis 114.

Figure 2A:
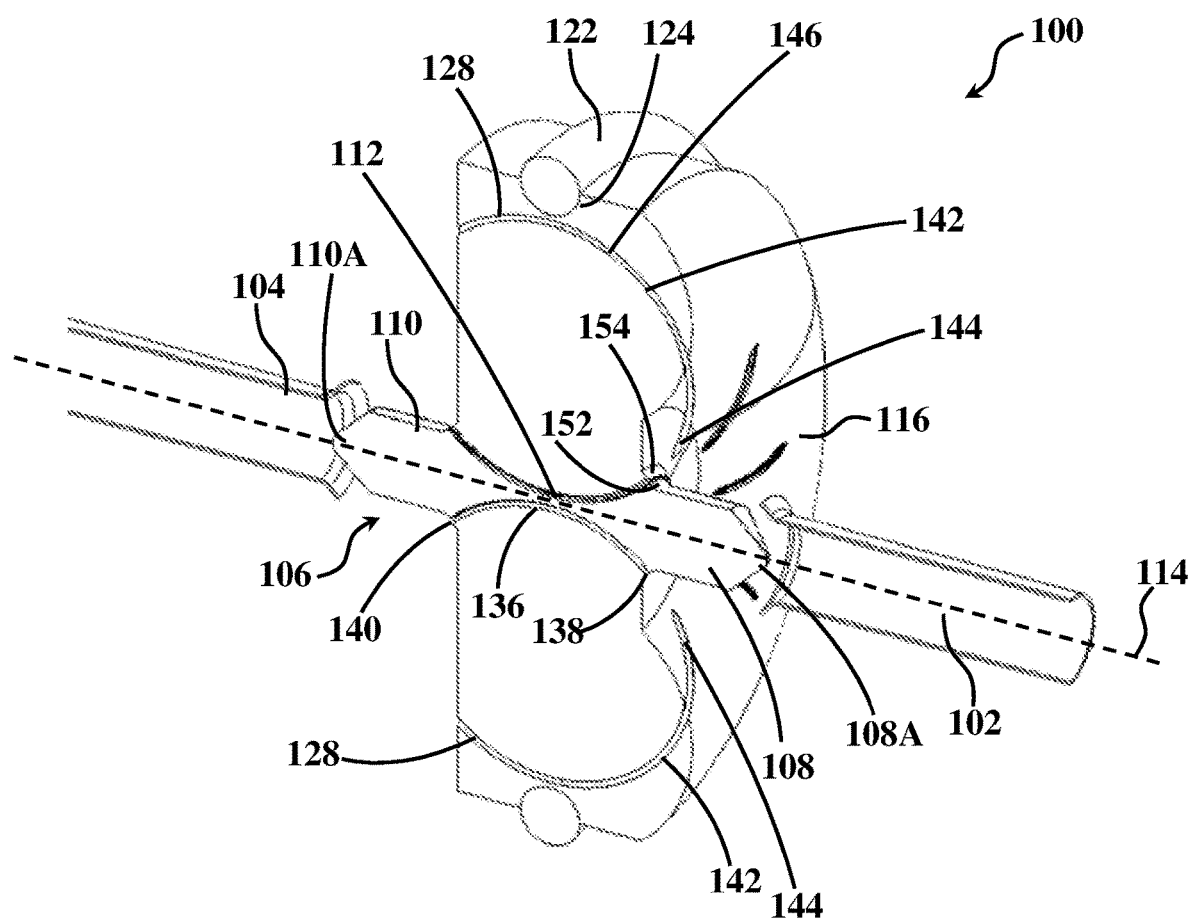
FIGS. 2A-2H are schematic representations of the sequence of operations for joining together stumps of a cut tubular organs by the use of the assembly of FIG. 1. of these figures.
Figure 2B:
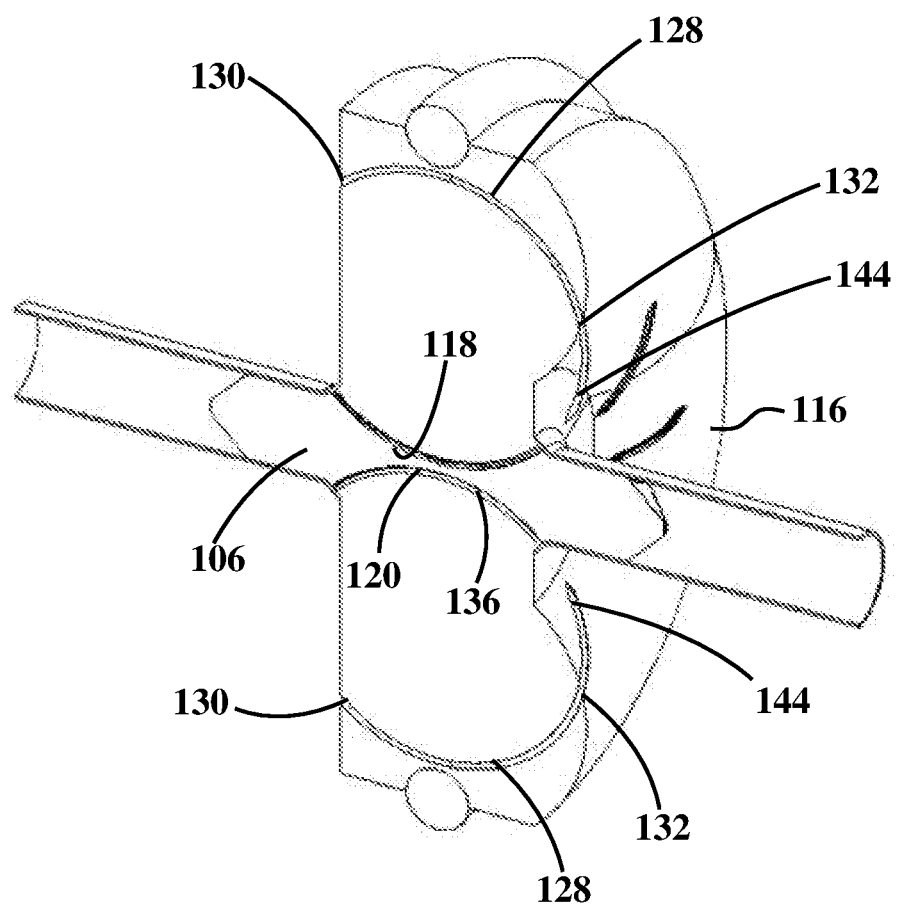

The generally cylindrical structure of axial projections 108, 110 and the tapered ends 108A, 110A facilitate the coupling of the axial projections with the stumps of a cut tubular organ 102, 104, respectively, by stretching the stump walls over the external face of the axial projections 108, 110, as seen in FIG. 2B. In this example the entire face of the axial projections 108, 110 together with the slanted surface 150, to be described below, serves as a stump-engaging portion. However, this is but an example, and in other cases (not shown) the stump engaging portion may only be at a distal part of the axial projections.

Surrounding the core member 106 is an external body 116 that has a generally annular or doughnut-like shape with a central void that accommodates said central segment 112. External body 116 and the central segment 112 of core member 106 jointly define the central part 105. The internal faces 118 of the external body 116 are tightly associated with the external face 120 of central segment 112 and, accordingly, have a generally convex cross-sectional profile on its inner face. External body 116 consists of two sub-units 116A, 116B, each constituting one half slice of the generally doughnut shaped body 116. The two sub-units 116A, 116B are held together by an annular integration-retaining member 122 that is accommodated within a peripheral groove 124. The integration-retaining member 122 may be a rigid ring or may be made of elastomeric material. As can be seen, the external body 116 includes the peripheral, axially orientated recess 126 that facilitates cutting of the integration-retaining member 122. Once the external body 116 disintegrates into two separate sub-units 116A, 116B, these can then be separated from the central segment 112 of the core member 106, as will also be described below.

Formed at the interface between the central segment 112 of core member 106 and internal face 118 of external body 116 is a first tunnel 136 extending between two openings including first inlet 138 and first outlet 140, in axial separation from one another. Defined within external body 116 are second tunnels 128 with openings 130, 132 in the opposite faces of the external body, which openings include a second inlet 130 and second outlet 132.

Accommodated within second tunnel 128 is suturing needle 142 with its front end 144 projecting out of second outlet 132. The needle has an intrinsic arched curvature that provides a trajectory guiding the tip 144 into first inlet 138.

Figure 2C:
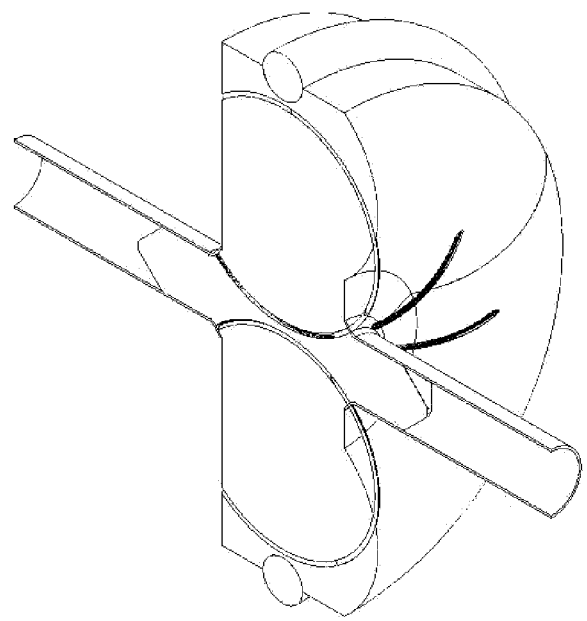
Figure 2D:
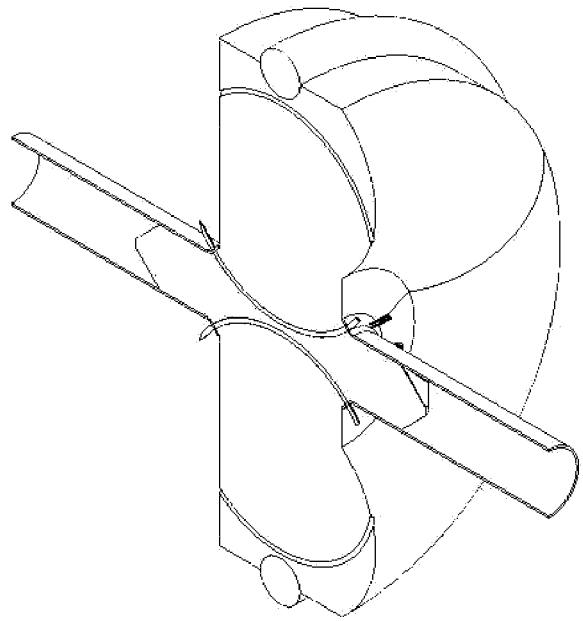
Figure 2E:
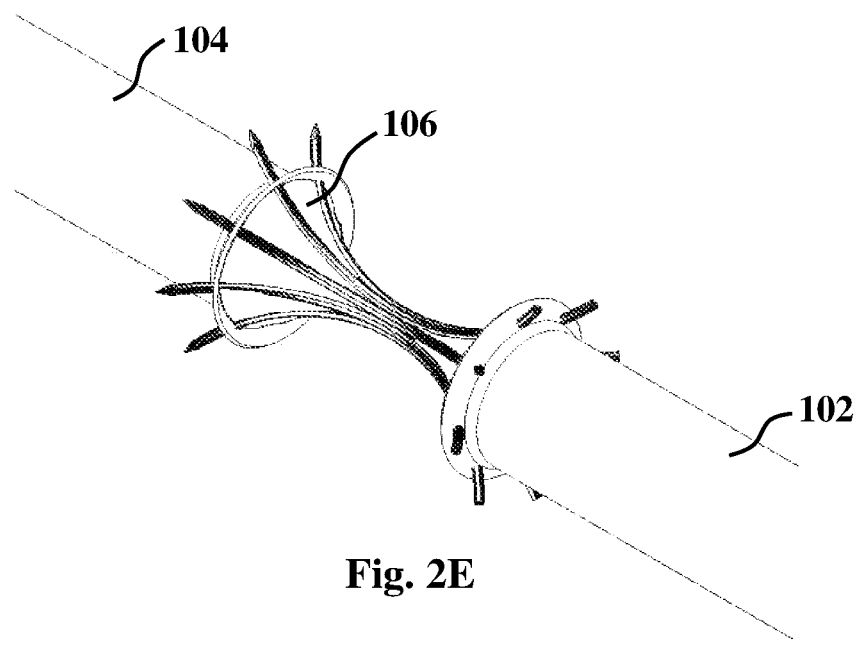

In this embodiment, each first tunnel and its corresponding second tunnel, that form together a tunnels' pair, have the curvature that defines an arch of a common circle, as can be seen in FIGS. 2A-2D. The needle has the same curvature and accordingly the trajectory traces the circle's circumference, as can be seen in FIG. 2C.

In the embodiment shown, the needle is already accommodated within the second tunnels, although it is also possible to introduce these needles into the second tunnels, immediately prior to or during the anastomosis procedure. The needles, as noted above, are part of a suturing unit that includes also a suturing thread. The thread is linked to the rear end 146 of needle 142, removed for ease of illustration.

Formed at the interface between the axial projection and the central segments of the core member 106 is a radially diverging surface 150 which is defined jointly by a portion 152 of the axial projection and another portion 154 of the external body, whereby the first inlet 138 and first outlet 140 of the first tunnel 136 are at the mid-portion of this slanted surface 150.

The sequence of operation is shown in FIGS. 2A-2H. In a first step, seen in FIG. 2A, the axial projections 108, 110 are engaged with respect to the two stumps 102, 104 and the stump walls thereof are pulled over the external surface until the end portion of the stump walls comes to lie over the two openings 138, 140, to a suturing state as can be seen in FIG. 2B. The needles 142 can then be gradually extracted out of the second tunnel 128 and its tip 144 thus penetrates through an end portion of the stump wall of the cut vessel before entering first inlet 138, as can be seen in FIG. 2C. Further movement of the needle can be manipulated (for example, by the use of tweezers) until the tip 144 exits through outlet 140, penetrating in this manner through an end portion of the stump walls of the cut tubular organ.

In a subsequent step, the integration-retaining member 122 is cut, the sub-units 116A, 116B are removed, thereby exposing the entire length of the first tunnels and hence frees their contents. In this procedural example, the sub-units 116A, 116B are removed whilst the needles are still within the first tunnel. However, it is also possible to first continue to extract the needles out of the first tunnels entirely and then the removal of sub-units 116A, 116B will expose suturing thread that extends between the two stumps.

Figure 2F:
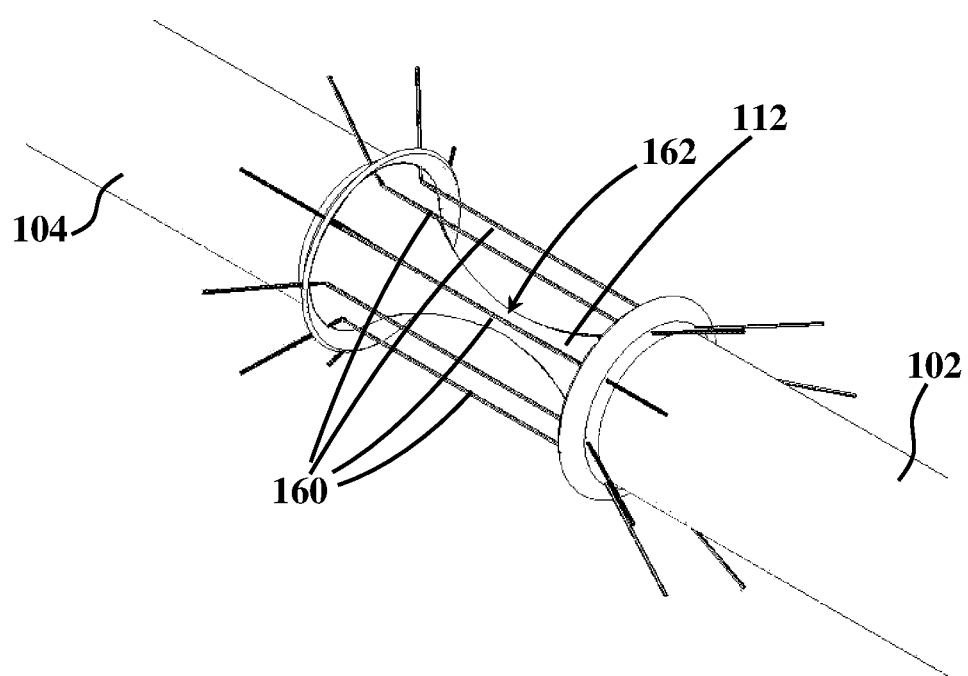
Figure 2G:
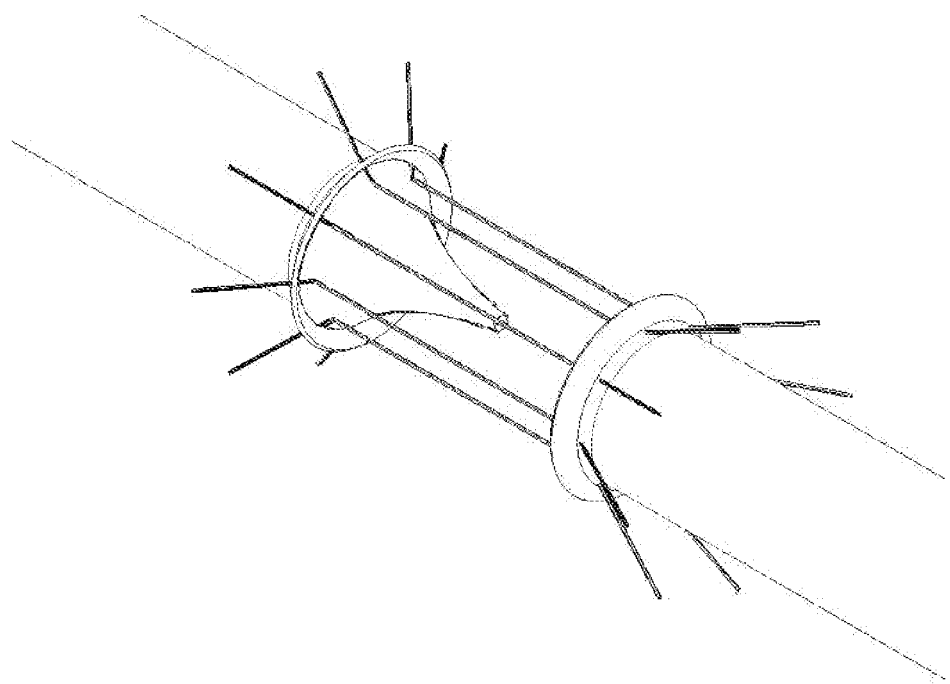

In the sequence of operations shown in these Figures, in the next step, the needles are continued to be pulled through, after removal of sub-units 116A, 116B, leading to the situation seen in FIG. 2F, whereby the two stumps 102, 104 are linked by a plurality of suturing threads 160.

At first, the central segment 112 still remains in situ. It has a relatively narrow mid-point 162, which can then be cut, e.g. by surgical scissors, and each cut half can then be removed, the sequence represented in FIGS. 2G and 2H. The sutures can then be pulled together, thus joining the two stumps.

Figure 2H:
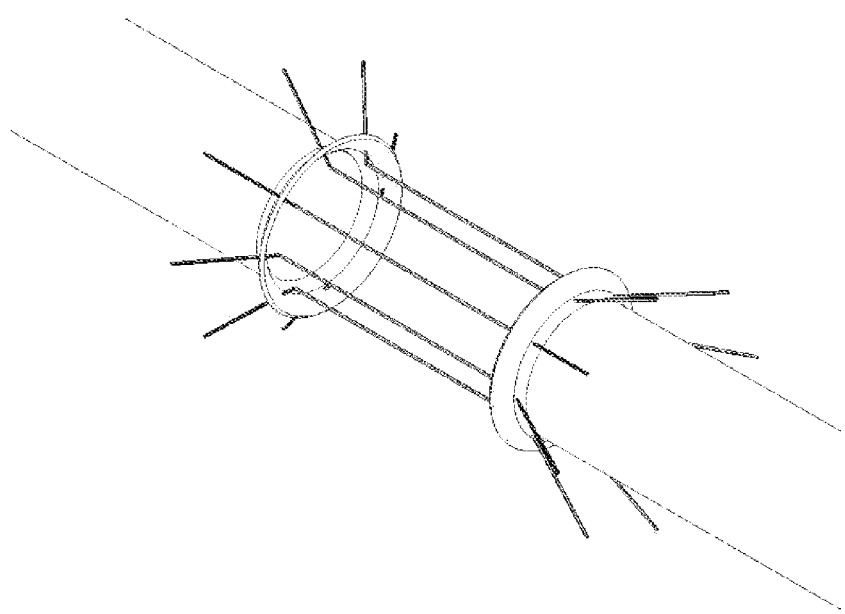
Figure 3A:
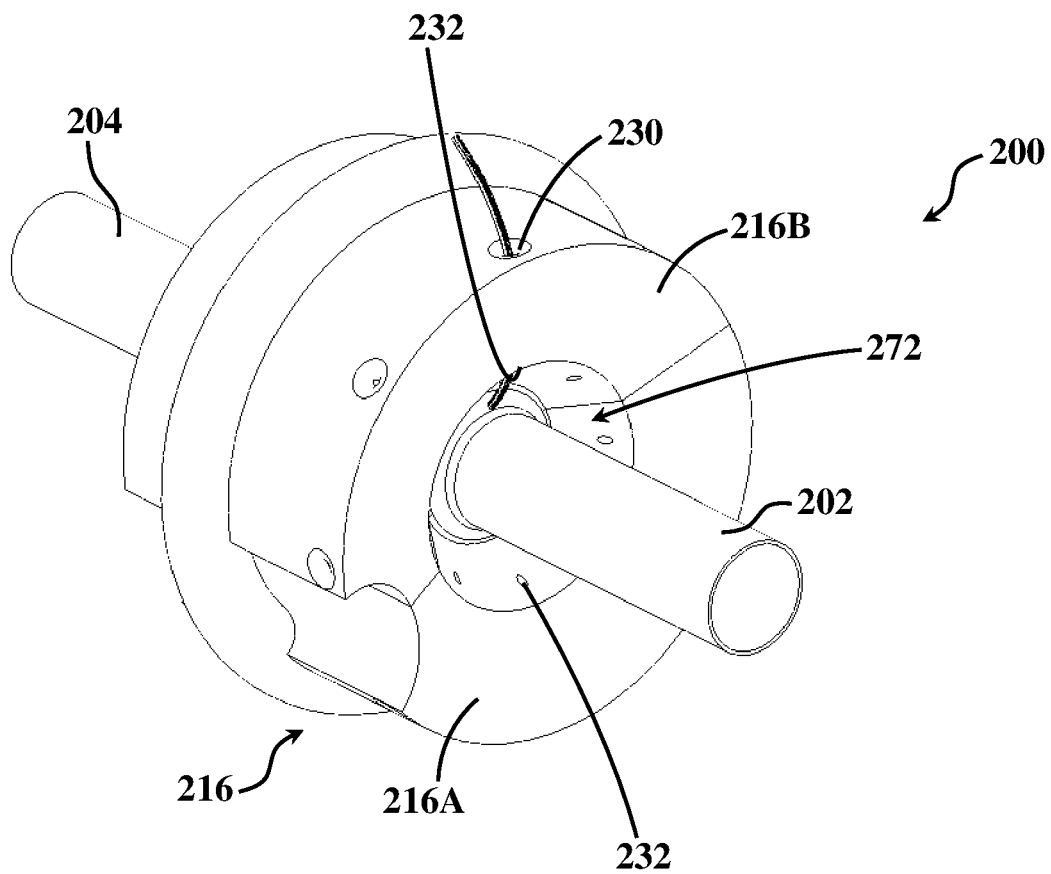
FIGS. 3A and 3B are schematic isometric representations of an anastomosis assembly according to another bored embodiment of this disclosure.
Figure 3B:
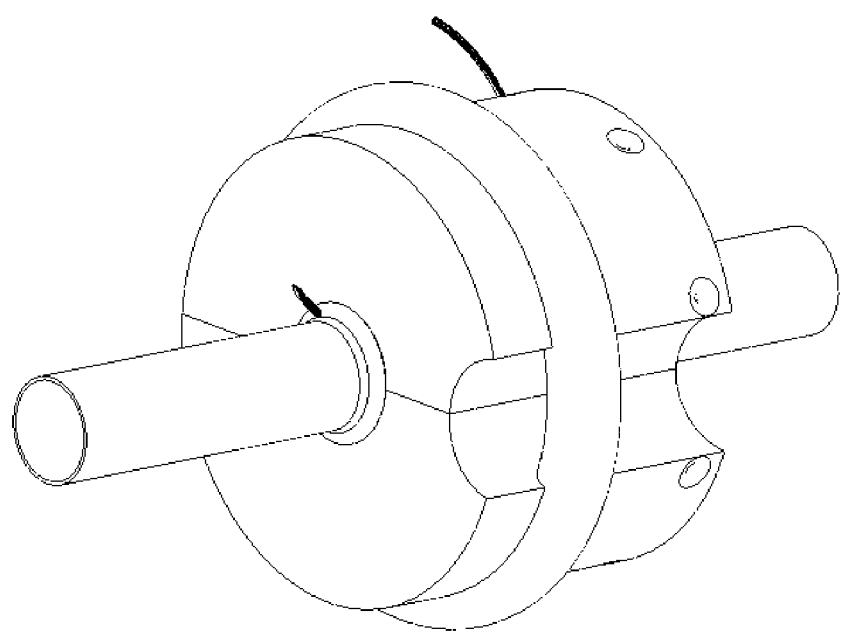
Figure 4:
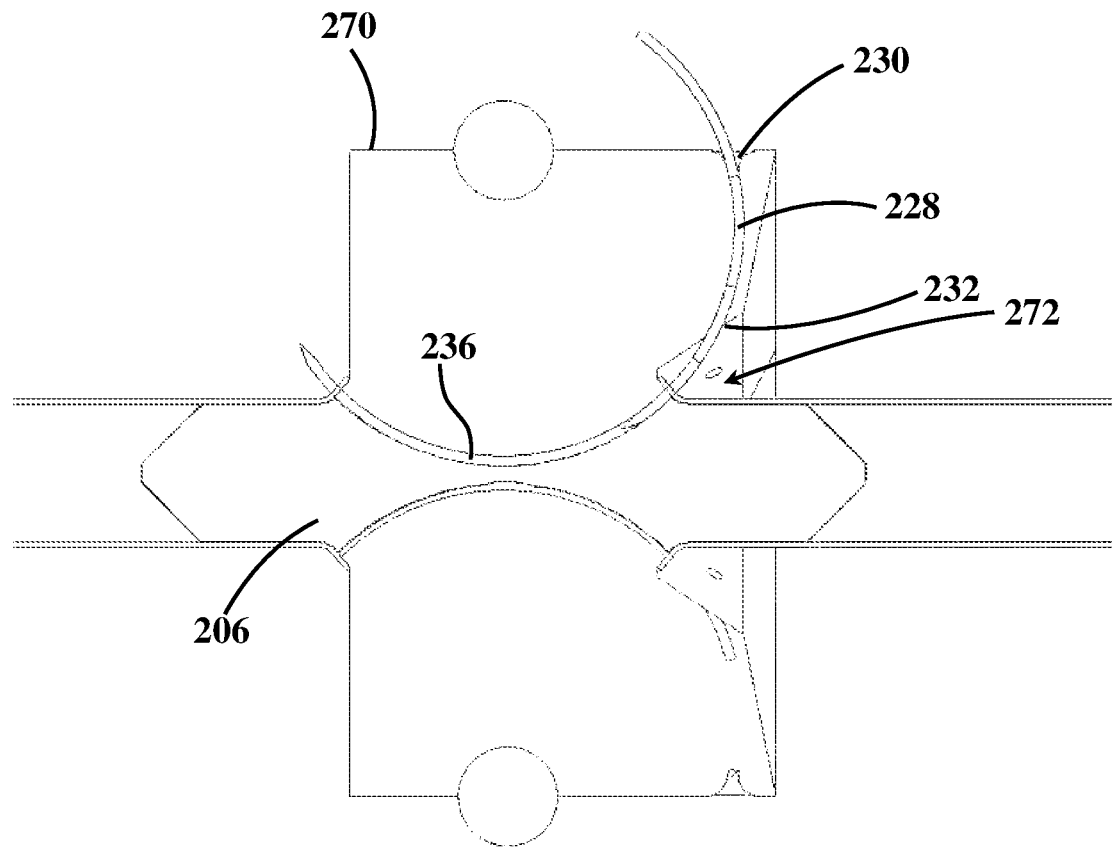
FIG. 4 shows a longitudinal cross section through the anastomosis assembly of FIGS. 3A and 3B.

Reference is now being made to FIGS. 3A, 3B and 4 providing a schematic illustration of another bored embodiment according to this disclosure. In these Figures, like elements to those of the embodiments shown in FIGS. 1-2H have been given like reference numerals, shifted by a hundred. Thus, by way of example, external body 216 and its two sub-units 216A, 216B, are functionally equivalent to external body 116 and its two sub-units 116A, 116B.

The main difference is in the second tunnel 228, which extends from second inlet 230 in the peripheral face 270 to an outlet proximal to the core member and has a generally radial orientation, unlike the more axially orientated second tunnel in the embodiment of FIGS. 1-2H. Also, the outlet 232 opens into space 272, defined between external body 216 and the core member 206, in a generally radial orientation. As can also be seen, the second inlets have a generally funnel-like configuration and allow easy insertion of the needle. Thus, this embodiment is particularly suitable for use of a single suturing unit in the anastomosis procedure and after passing the needle and the thread through one tunnels' pair (that consists of first tunnel 236 and second tunnel 228), it can be pulled out and inserted into a consecutive tunnels' pair.

Referring now to FIGS. 5-6C, seen is an assembly 1000 according to the open channel embodiment of this disclosure, including a device 1002, a plurality of suturing needles 1004, and a sliding insert 1006. The device 1002 has an axial symmetry about axis 1008 and is mirror symmetric about the midline 1010, with two integral mirror-symmetric parts 1002A and 1002B. The suturing needles form pairs, the two members of the pair being linked to one another by a suturing thread, of which one 1012 is shown schematically in FIG. 5, the others not shown for ease of illustration. Each of the suturing needles is coupled at its rear end portion 1014 to the suturing thread. Such pair of needles and the associated thread constitute together a suturing unit.

The device 1002 has two opposite axial projections 1020, having a tapered end 1022 and a generally cylindrical portion 1024 and a frusto-conical portion 1026. In use a stump (not shown) of a tubular organ, a blood or a lymph vessel, is pulled over this axial projection, and pulled all or most of the way over surface of the frusto-conical portion 1026; thus, the entire external surface of the axial projection constitutes the stump-engaging portion of the device.

A plurality of generally axially extending open channels 1028 are defined in device 1002, each with side walls and a curved bottom wall 1030. Each of these open channels extends from one end at the central body to a second end in the stump-engaging portion of one of the axial projections. The suturing needle 1004 that have a curvature to match that of bottom wall 1030 is accommodated within the channel 1028 with its pointed portion 1032 directed towards the second end being within the channel. For suturing, the needle is slid within the channel, and in this manner when the stump (not shown) is fitted over the stump-engaging portion, the needle penetrates the stump wall, pulling the suturing thread after it. FIGS. 5 and 6B-6C show one needle with its tip portion 1032 already projecting out of the second end 1036, while the others are still in their initial state with their tip portions accommodated within the channels.

Typically, once a needle penetrate through the stump walls, it can be further pulled, for example, by the use of forceps.

The needle may be slid in a forward direction in an arched trajectory, tracing the curvature of the channel so as to penetrate through the stump wall either by pushing on the rear end portion 1014 or by the use of a sliding insert 1006. The sliding insert 1006 has a width to match that of the open channel 1028 with its edge 1040 having a curvature to match that of the bottom wall 1030. The edge may be textured, may be layered with a friction-increasing material, e.g. an elastomer, or said insert may be made entirely from a material that induces sufficient friction to thereby cause, through its rotation about location 1042, the forward-directed sliding of the needle. The insert may, alternatively, be manipulated by a forceps, attached to a manipulation rod, etc.

As can be seen in FIG. 5, the pair of suturing needles of a suturing unit are accommodated in opposite (with respect to midline 1010) open channels. Thus, this arrangement causes that eventually opposite portions of the two stumps will be properly joined to one another.

Device 1002 has two annular depressions 1046, which can accommodate a retaining element 1122, for example a band or a ring made of elastomeric material, to thereby retain the needles within the channels. Once the two stumps are linked by the still sleek suturing threads this retaining element 1122 can be cut or otherwise removed to free the threads from the channels and remove the device to complete the suturing procedure.

Figure 7A:
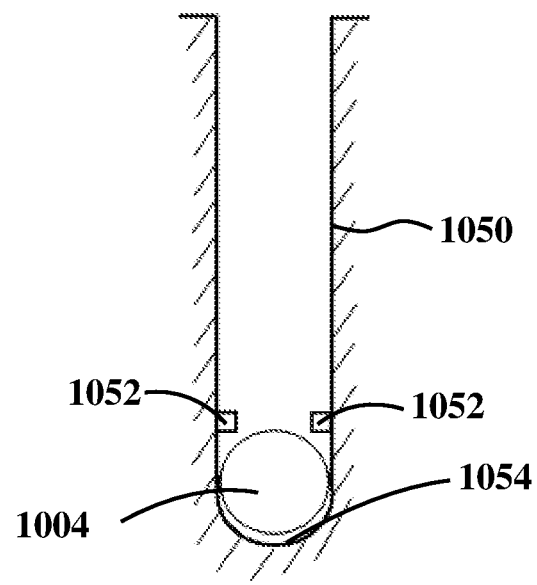
FIGS. 7A-7B are schematic radial cross-sections through a portion of the device showing exemplary embodiments of the open channels configured to retain the suturing needle within the channel while permitting the suturing thread to be freed from the channel in an unhindered manner.

FIG. 7A shows an alternative configuration of the open channel, which permits the retention of the needle within the channel while permitting unhindered removal of the suturing thread. Channel 1050 of this embodiment has a uniform width but has two opposite bulges 1052, which have the effect of arresting the needle at the bottom end 1054 of the channel. The suturing thread has a diameter smaller than the span between the bulges 1052 and, once the needle passes fully out of the channel, the remaining thread can be easily freed from the channel.

Figure 7B:
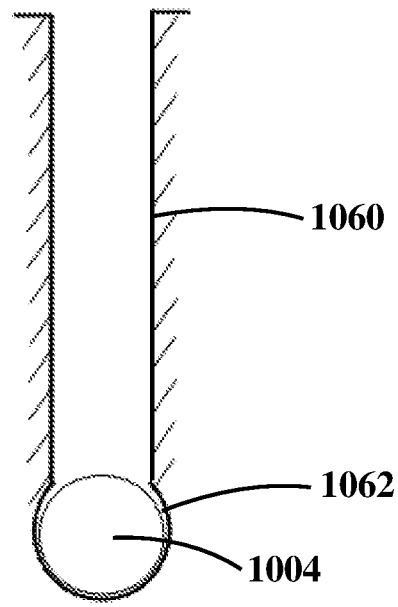

FIG. 7B shows another alternative configuration of a channel 1060 that has a uniform width, with a wider bottom portion 1062 that is sized to snugly accommodate the needle 1004. While the channel has a width narrower than the diameter of the needle 1004 which is, thus, retained within bottom portion 1062, it permits the unhindered removal of the suturing thread similarly to the embodiment of FIG. 7B.

The invention claimed is:

1. An anastomosis assembly for joining one stump of a cut tubular organ to another comprising: a device having a body with a longitudinal axis and two opposite axial projections, each of which being configured for insertion into a stump to be joined to another stump and to permit the stump walls to be pulled over a stump-engaging portion of the external surface of the axial projections; a plurality of curved, open needle-guiding channels, each of which extending in a general axial direction between a first end and a second end defined in the stump-engaging portion of one of the axial projections and configured for receiving a suturing needle, having a pointed front and a rear linked to a suturing thread, wherein each open needle-guiding channel is configured to guide the pointed front of the suturing needle to pierce through stump walls; and each of the two opposite axial projections comprises a retaining element in the form of an elastic element, fitted directly over the open needle-guiding channels within a circumferential groove defined on the surface of the axial projection directly over the open needle-guiding channels, the retaining element is configured for retaining the suturing needles within the open needle-channels before and during the needles movement in the open needle-guiding channels to pierce through stump walls, and the retaining element is configured to be cut or broken to permit freeing of the suturing threads from the device upon the removal of the retaining element.

2. The assembly of claim 1, comprising a plurality of suturing needles accommodated within the needle-guiding channels.

3. The assembly of claim 1, wherein each of the needle-guiding channels extends between the body and the stump-engaging portion of one of the two opposite axial projections.

4. The assembly of claim 1, wherein the device has a mirror symmetry about a plane perpendicular to the longitudinal axis.

5. The assembly of claim 4, wherein
each of the needle-guiding channels extends between the body and the stump-engaging portion of one of the two opposite axial projections, and wherein suturing threads extend between needles accommodated within pairs of oppositely disposed needle-guiding channels.

6. The assembly of claim 1, wherein the open needle-guiding channels are configured for retaining the suturing needles but permitting release of the suturing threads.

7. The assembly of claim 1, wherein the plurality of curved, open needle-guiding channels are axially-extending radially-oriented and each has side walls and a curved bottom wall; and further comprising a plurality of suturing units, each unit comprising a pair of the suturing needles linked to one another at their rear portion by the suturing thread, each needle having a pointed front portion; and each suturing needle of a suturing unit being accommodated in one of the open needle-guiding channels opposite with respect to a plane of mirror symmetry to the other, with its pointed front portion in the direction of said second end, each of the needles being slidable within one of the open needle-guiding channels and guided by the bottom walls to pierce through the stump walls once the stump walls are pulled over the stump-engaging portion.

8. The assembly of claim 7, wherein the rear portion of each needle projects out of the first end of one of the open needle-guiding channels and each needle can be slid in a general axial direction by pushing said rear portion.

9. The assembly of claim 7, wherein sliding of each of the needles is achievable by means of a sliding insert insertable into the open needle-guiding channels.

10. The assembly of claim 7, wherein the open needle-guiding channels are configured for retaining the suturing needles but permitting release of the suturing threads.

\* \* \* \* \*